(12) United States Patent
Fortin et al.

(10) Patent No.: US 9,072,544 B2
(45) Date of Patent: Jul. 7, 2015

(54) DEVICE FOR DYNAMIC POSTERIOR STABILISATION MATCHING THE ANATOMIC LORDOSIS

(75) Inventors: Frédéric Fortin, Pessac (FR); Johann Robin, Bègles (FR); Olivier Gilles, Pessac (FR); Brice Sennequier, Pessac (FR)

(73) Assignee: BIOSPINE Implants, Pessac (FR)

( * ) Notice: Subject to any disclaimer, the term of this patent is extended or adjusted under 35 U.S.C. 154(b) by 452 days.

(21) Appl. No.: 12/993,976

(22) PCT Filed: May 20, 2009

(86) PCT No.: PCT/FR2009/000584
§ 371 (c)(1),
(2), (4) Date: Mar. 7, 2011

(87) PCT Pub. No.: WO2009/153431
PCT Pub. Date: Dec. 23, 2009

(65) Prior Publication Data
US 2011/0152935 A1    Jun. 23, 2011

(30) Foreign Application Priority Data

May 23, 2008   (FR) ...................................... 08 02807

(51) Int. Cl.
*A61B 17/70*   (2006.01)
(52) U.S. Cl.
CPC ......... *A61B 17/7023* (2013.01); *A61B 17/7025* (2013.01); *A61B 17/7031* (2013.01)

(58) Field of Classification Search
CPC ........... A61B 17/7005; A61B 17/7011; A61B 17/7019; A61B 17/7023; A61B 17/7025; A61B 17/7026; A61B 17/7031
USPC ........................................... 606/256–260, 264
See application file for complete search history.

(56) References Cited

U.S. PATENT DOCUMENTS

| | | | |
|---|---|---|---|
| 5,375,823 A * | 12/1994 | Navas | 623/17.15 |
| 6,241,730 B1 * | 6/2001 | Alby | 606/256 |
| 7,763,048 B2 * | 7/2010 | Fortin et al. | 606/246 |
| 7,785,350 B2 * | 8/2010 | Eckhardt et al. | 606/254 |
| 8,231,657 B2 * | 7/2012 | Eckhardt et al. | 606/254 |
| 8,449,576 B2 * | 5/2013 | Lechmann et al. | 606/257 |
| 8,506,599 B2 * | 8/2013 | Jackson | 606/264 |
| 2005/0165396 A1 * | 7/2005 | Fortin et al. | 606/61 |
| 2007/0149909 A1 * | 6/2007 | Fortin et al. | 602/32 |
| 2008/0147078 A1 * | 6/2008 | Francis et al. | 606/102 |

FOREIGN PATENT DOCUMENTS

FR           2869524 A1 *  11/2005
WO     WO 03007828 A1 *   1/2003

* cited by examiner

*Primary Examiner* — Ellen C Hammond
(74) *Attorney, Agent, or Firm* — Hodgson Russ LLP

(57) ABSTRACT

The a device is provided for dynamic posterior stabilization. The device combines includes a mobile piston rod with a piston head at an end thereof; a viscoelastic shock-absorbing unit having a convex surface; a fixed rod defining an angle relative to an axis of a casing and the fixed rod including, at an end thereof, a concave surface; a viscoelastic ring; and wherein the viscoelastic components are contained within the casing.

6 Claims, 5 Drawing Sheets

Figure 1:
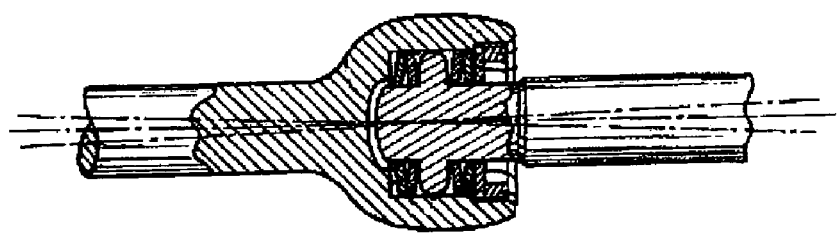

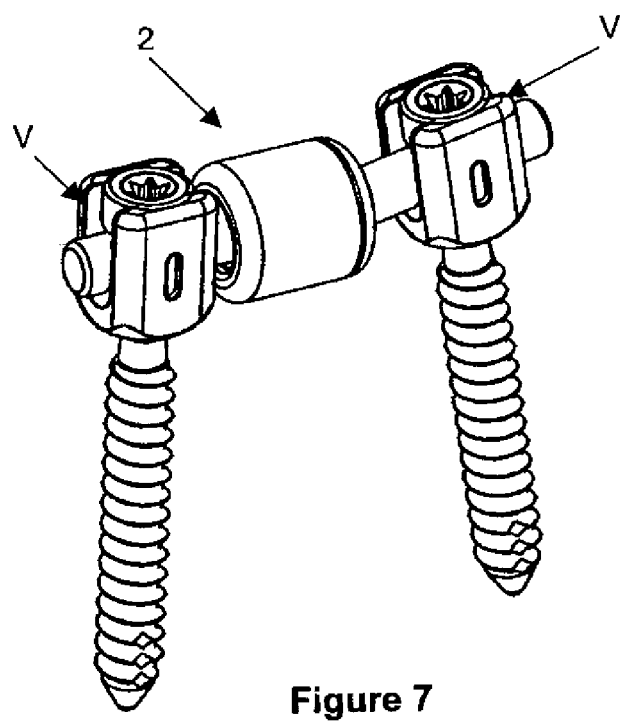
Figure 7
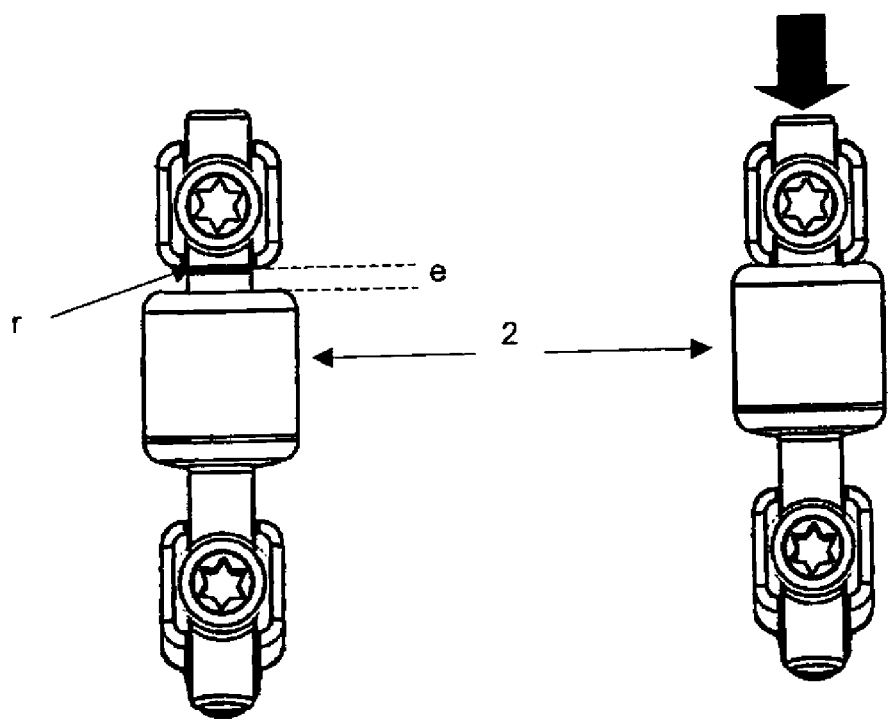
Figure 8
Figure 9

DEVICE FOR DYNAMIC POSTERIOR STABILISATION MATCHING THE ANATOMIC LORDOSIS

This application claims priority to French patent application 0802807, filed on May 23, 2008.

FIELD OF THE INVENTION

The invention relates to a dynamic posterior vertebral stabilization device conforming to the shape of the anatomical lordosis, which device is attached between two pedicular screws and which absorbs all the mechanical stresses and which allows a controlled mobility of the intervertebral segment.

This device will exhibit novel means with functional advantages superior to those of the prior art.

PRIOR ART

Numerous posterior vertebral attachment systems are known that rigidify a certain number of vertebrae depriving them of all mobility in order thus to make it possible to absorb all mechanical stresses. However, the first vertebra adjacent to this rigid block keeps all its mobility and this sudden discontinuity between the rigid block and this free vertebra very often causes an excessive stress on the connecting elements. The result of this is an acceleration in the degeneration of this level.

This problem has been only partially solved by semirigid systems designed to create an intermediate rigidity between the mobile vertebrae and the fixed vertebrae. These systems have the following drawbacks:

Either they work only in tension. This is the case with all the devices based on artificial ligaments. These systems are not very elastic and leave it to the judgment of the operator to adjust the tension thus randomizing the mechanical characteristics in particular in the tension/compression operating mode which concerns us most frequently.

Or they work in compression with a tension stop, which makes these devices ineffective when they have to assist movements in extension.

Whatever the case, none of the known devices entirely solves the problem posed, namely: to absorb the mechanical stresses that exist in tension/compression and in flexion to which two vertebrae can be subjected, while complying with the anatomical lordosis, and allowing ranges of movement compatible with the stresses of the human body.

Cited as the first priority will be the patent FR 2771280, a resilient vertebral connecting device consisting of two mobile rods connected by means of a shock-absorbing element made of metal materials of moderate elasticity and having a considerable rigidity. This device can in no circumstances have the same functions and the same flexibility as those obtained by the present invention. Its performance is limited and the mobility of the device is closer to that of a rigid metal rod than to the mobility that the present invention will provide.

Cited as a second priority will be the document No. EP 0669109 "Stabilisierung von benachbarten Rückenwirbeln".

This priority is a hollow polyurethane cylinder compressed between two pedicular screw heads, made from a stretched ligament which passes through the hollow cylinder and which is attached to the screws by clamping of the stoppers. In addition to the fact that there is no possibility of obliquity of the polyurethane cylinder which therefore does not comply with the anatomical lordosis; the latter is very stiff and allows very little mobility of the intervertebral segment. Our invention, on the other hand, is aimed at making the mobility of the treated intervertebral segment easier by making it tend toward a normal anatomical position (compliance with the lumbar lordosis angle).

Cited as a third, more recent, priority will be the application PCT WO03007828 which describes and claims "a flexible vertebral connecting device".

This priority, although improving the prior art of metal devices, does not completely solve the problem that will be solved by the present invention in which the means and functions put in place very markedly improve the functionalities.

This is what the present invention proposes to do by putting in place novel means necessary for obtaining the expected results.

Figure 2:
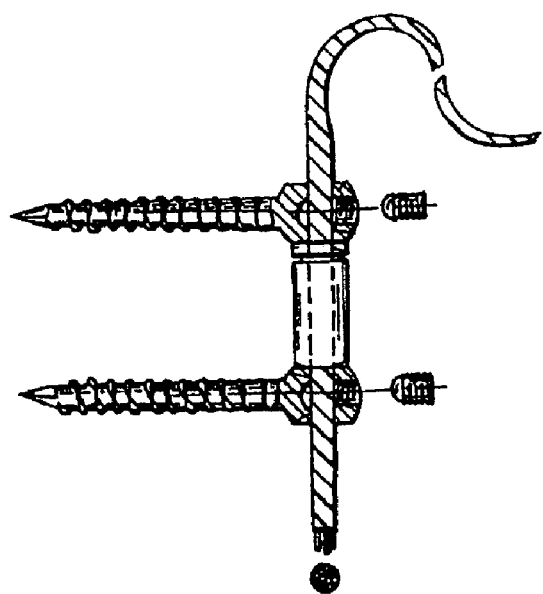
Figure 3:
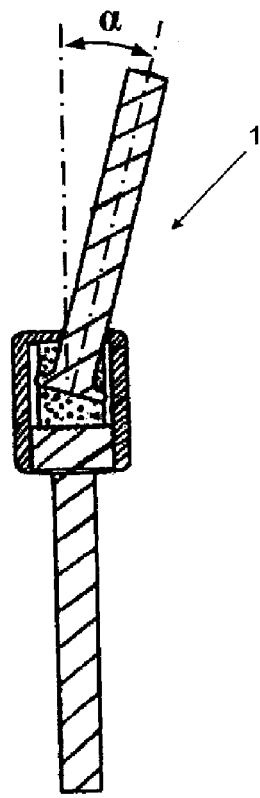
Figure 4:
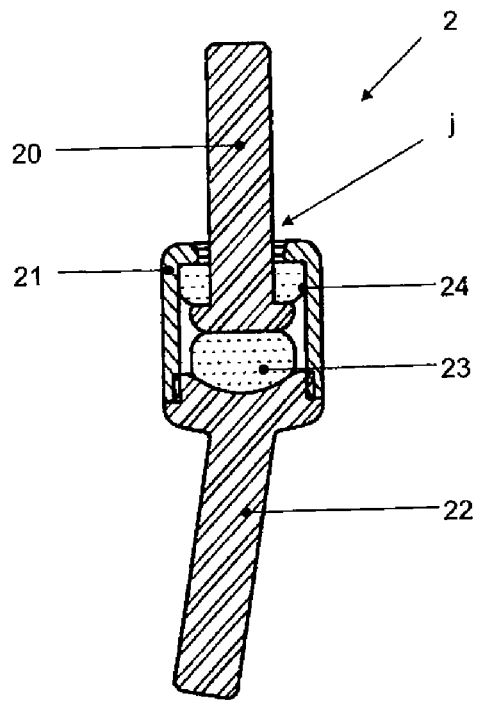
Figure 4D:
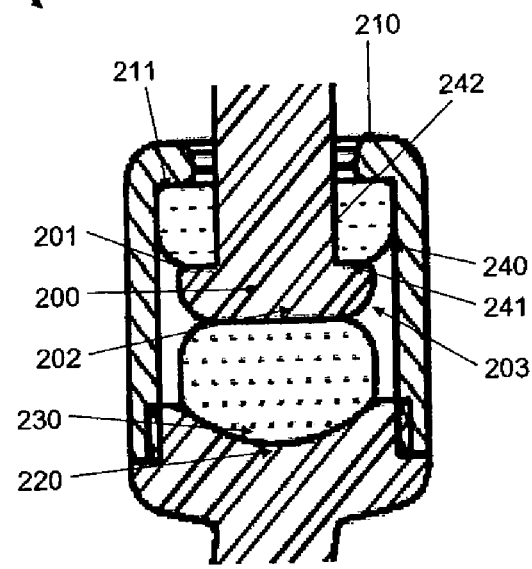
Figure 5:
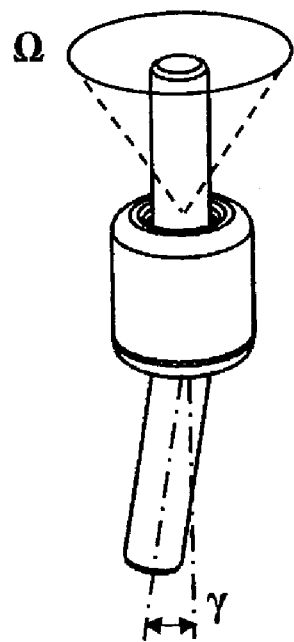
Figure 6:
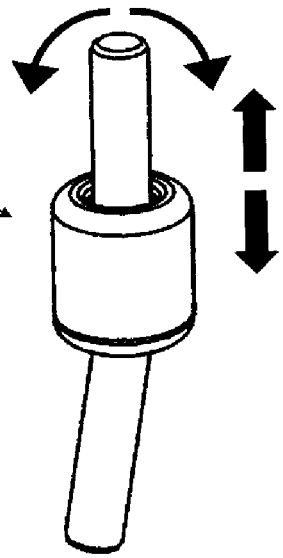
Figures 10, 11:
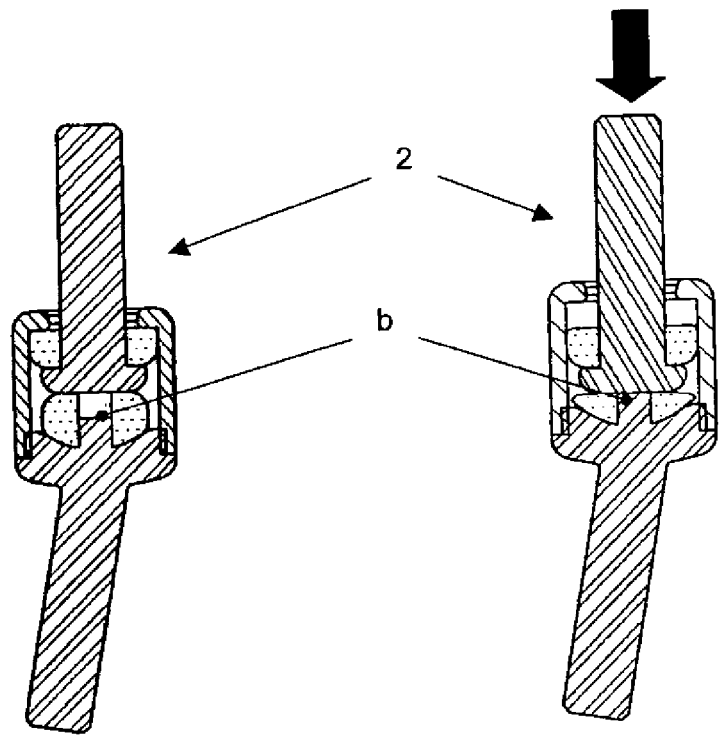
Figure 12:
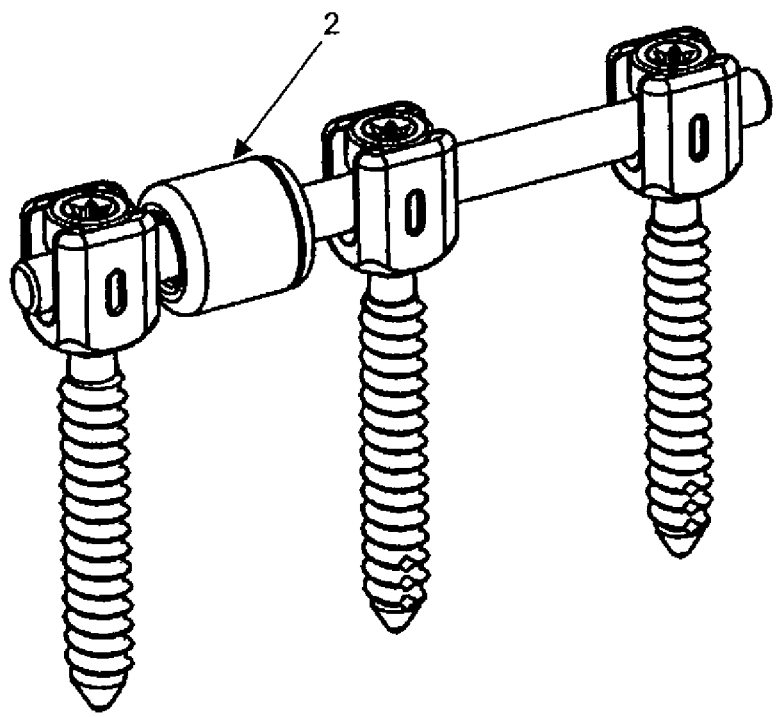
Figure 13:
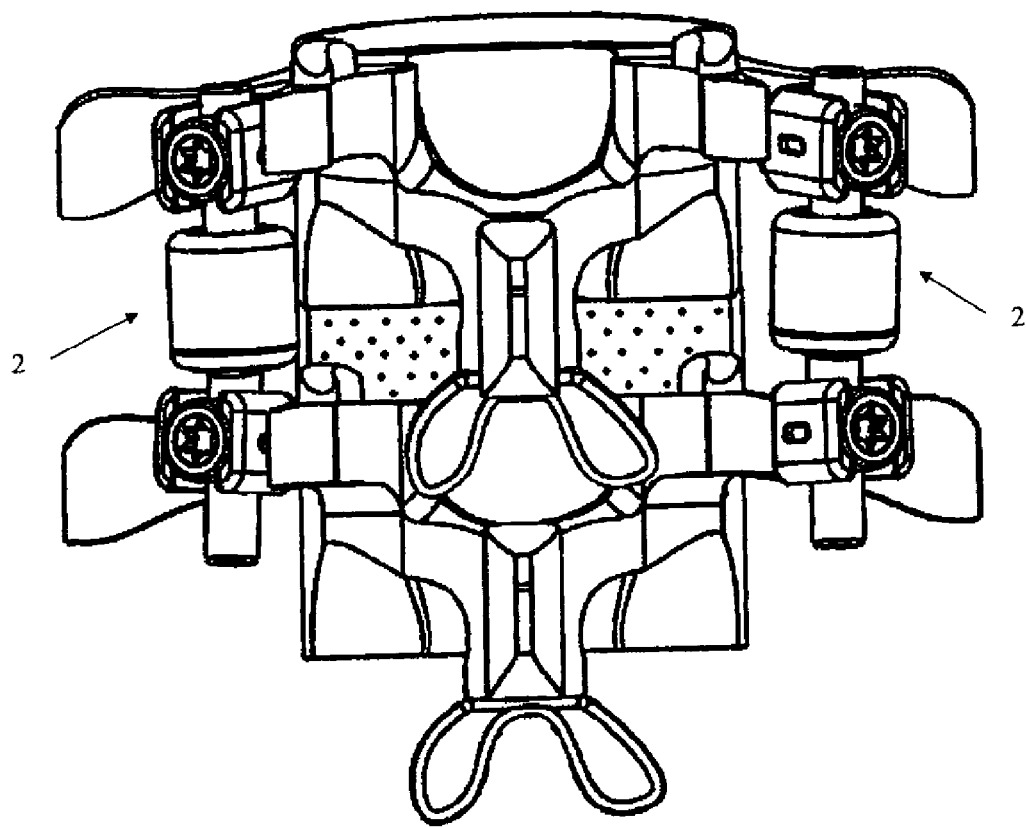

The figures used for the comprehension of the invention are:

FIG. 1, plate 1/5, a view in section of the device corresponding to patent FR 2771280 (prior art: entirely mechanical means), FIG. 2, plate 1/5, a view in section of the document No. EP 0669109, FIG. 3, plate 1/5, a view in section of the closest device of application PCT WO/03007828 (prior art), FIG. 4, plate 2/5, a view in section of the novel device with its means of application, FIG. 4d, plate 2/5, a view in detail of the novel device with its means of application, FIG. 5, plate 2/5, a view in perspective of the novel device illustrating its multiaxiality possibilities, FIG. 6, plate 2/5, a view in perspective of the novel device working in flexion and tension-compression mode, FIG. 7, plate 3/5, a view in perspective of the novel device mounted on pedicular screws, FIG. 8, plate 3/5, a rear view of the novel device mounted on pedicular screws with the positioning mark, FIG. 9, plate 3/5, a rear view of the novel device mounted on pedicular screws showing the bottom position limit in compression, FIGS. 10 and 11, plate 4/5, a view in section of the novel device comprising a safety stop, FIG. 10 device at rest and FIG. 11 device in compression, FIG. 12, plate 4/5, a view of a novel device mounted on three pedicular screws attached to adjacent bodies, FIG. 13, plate 5/5, a view of two devices that are the subject of the invention mounted on the spinal column.

IN THE EMBODIMENT OF THE CLOSEST PRIOR ART

The device (1) closest to the novel device (2) that is the subject of the invention comprises:

A set of rigid means combined with viscoelastic means, the first of which transmit the forces and the second absorb the dynamic stresses.

The rigid means consist of three elements:
a piston rod placed in the top portion
a fixed rod in the bottom portion
a cap enclosing all of the viscoelastic means.

The biocompatible viscoelastic means, preferably made of silicone or of polyurethane, consist:
of an obliquely truncated viscoelastic solid cylinder
of an obliquely truncated viscoelastic ring, the faces of which come into contact with the piston of the piston rod.

The device 1 is capable of operating with the rods and one of them, the piston rod, moves multiaxially with a small angle of movement and determined ranges of movement.

There is an orifice placed at one of the ends of the cap which allows a multiaxial range of movement of the piston rod of the device 1.

The shape of this orifice is defined depending on the planned ranges of movement. The piston rod can therefore work in tension, compression with a predetermined angle α, the piston rod then forming with the fixed rod a given angle depending on the shape of the orifice.

This priority has drawbacks that are too great to entirely solve the problem posed.

On the one hand, the smallest section of the obliquely truncated ring sustains too many strains under the action of the mechanical stresses and consequently deteriorates rapidly.

On the other hand, the piston rod which forms an angle α with the fixed rod in the neutral position butts against the metal cap during considerable stresses which limits the angular ranges of movement and therefore the mobility of the patient. The section of the obliquely truncated ring has zones with thin walls resulting in the fact that the oblique ring can in no circumstances withstand the movements of the piston rod toward the edge of the cap. This generates wear debris, which will get worse and which is very harmful to the longevity of the device, thus to the health of the patient. Note also the absence of return force which means that the dynamic response of the device 1, unsuited to the biomechanics of the spinal column, becomes harmful. That is why this priority cannot be used to entirely solve our problem.

IN A PREFERRED EMBODIMENT OF THE INVENTION

The device 2 is a combination of rigid means and of viscoelastic means allowing the device 2 to form an angle γ in the neutral position between its two attachment elements to the pedicular screws and to apply a permanent elastic return force around this position while absorbing the compression and flexion forces applied to the pedicular screws.

The device 2 comprises:

a mobile piston rod 20 comprising a piston head 200 at its end a viscoelastic shock-absorbing pad 23 comprising a convex face 230 a fixed rod 22 forming an angle γ relative to the axis of the cap 21 which comprises, at the end situated inside the device 2, a concave surface 220 which conforms perfectly to the shape of the convex face 230 of the viscoelastic shock-absorbing pad 23 a viscoelastic ring 24 housed inside the cap 21 enclosing the viscoelastic means 23 and 24.

The assembly clearances of this ring with respect to the piston rod 20 and to the cap 21 have been optimized on the basis of endurance tests in order to maintain a satisfactory elastic return.

The cap 21 comprises, in its top portion, a conical orifice 210, the conicity of which allows the angular ranges of movement of the mobile piston rod 20 that can also serve as a stop without applying concentration of stress while limiting the angular ranges of movement of the rod. The internal face of the cone 211 also makes it possible to offer the largest possible contact surface to the viscoelastic ring 24 which rests perfectly on this face of the cap and thus limiting the stresses in the ring 24.

The device 2 is attached to the pedicular screws by the ends of the rods 20 and 22. These two rods form between them an angle γ, the neutral position of the unstressed device. This angle γ reproduces the angle of the anatomical lordosis of the spinal column, a position of perfect equilibrium, around which the device 2 will always tend to return by virtue of an elastic return force applied by the ring and the viscoelastic pad 24 and 23, and will do so irrespective of the dynamic stresses and movements that are imposed on the rod 20.

The device 2 comprises the fixed rod 22 which forms the angle γ relative to the cap 21 and to the neutral position of the mobile piston rod 20. The piston rod 20 is positioned in the axis of the cap and moves in both directions along this axis while compressing the viscoelastic means 23 by virtue of the bottom face 202 of the piston head 200 during the compression and flexion movements and by also compressing the viscoelastic ring 24 by virtue of the top face of the piston 201 during the tension and flexion movements.

The axial movement of the mobile piston rod 20 can be combined with angular movements Ω of this same rod by virtue of the contact between the two faces 201 and 202 of the piston 200.

When the device is at rest, the absence of clearance causes stressless contacts between the piston head 200 and the viscoelastic means 23 and 24 by virtue of the type of assembly carried out. The deformation of the viscoelastic means 23 and 24 allows the piston head 200 to adopt an angle around its neutral position depending on the stresses applied. Under mechanical stresses, the viscoelastic means 23 and 24 are then compressed over a portion of their surface and apply an elastic return force to the piston head 200 tending to return the rod 20 to the axis of the cap 21.

The piston 200 of the rod 20 has a knuckle 203 on its bottom face 202 which prevents creating beginnings of breakage of the viscoelastic shock-absorbing pad 23 when the piston 200 adopts an angle.

Similarly, the viscoelastic ring 24 has a knuckle 240 on its face 241 in order to limit the risks of initiating a break when the piston 200 adopts an angle.

This viscoelastic ring 24 also makes it possible to apply an elastic return force to the angular ranges of movement of the rod 20 by the possible deformation of its internal diameter 242. The possible deformations of the viscoelastic ring 24 allow the angular ranges of movement Ω of the rod 20 to be absorbed.

The geometry of the conical orifice 210 of the cap 21 makes it possible to limit the ranges of movement of the rods 20 inside a cone defined by an angle of polyaxiality Ω of the order of 15°.

At the travel limit, the mobile piston rod 20 comes into linear contact on the conical surface 210 and not in sporadic contact as was the case in the closest invention of the prior art (FIG. 3) which has the effect of reducing the concentrations of stresses on the piston rod 20.

When the device 2 is subjected to compression stresses, the bottom face 202 of the piston 200 will compress the viscoelastic element 23, the two faces in contact being flat in order to distribute the stresses over the totality of the surfaces in contact. The fixed rod 22 comprises, at the end situated inside the device 2, the concave surface 220 which conforms perfectly to the shape of the convex face 230 of the viscoelastic shock-absorbing pad 23.

The concentricity of these convex and concave faces which match perfectly allows centering of the viscoelastic element 23 with the rod 22 and the cap 21 so that the viscoelastic means 23 is perfectly centered inside the cap 21.

This design allows the viscoelastic element 23 to deform without coming into contact with the internal walls of the cap 21 while preventing friction and excess stresses that are extremely harmful to the longevity of the viscoelastic means 23.

Moreover, this centering by the concavity 220 and the convexity 230 of the fixed rod 22 and of the viscoelastic element 23 prevents all radial movement of the viscoelastic element 23 that could be caused by a flexing movement of the piston rod 20, the piston 200 applying an oblique pressure to the viscoelastic means 23.

This is why the operation of the device 2 is markedly improved relative to the device 1 that is more limited in its ranges of movement and in its service life.

The mobile piston rod 20 comprises a mark r (FIGS. 8 and 9) intended for a perfect positioning of the device 2. This mark r is aimed at by the operator when positioning the piston rod 20 and must be aligned with the bottom face of the pedicular screw heads V. This alignment makes it possible to maintain a distance e (of a few mm) between the top face of the cap 21 and the bottom face of the pedicular screw heads V, in order to limit the induced stresses and movements beyond this limit in the viscoelastic element 23.

If there should be dynamic stresses that are too high, the bottom face of the pedicular screw would butt against the top face of the cap 21 in order to limit the forces applied to the viscoelastic means of the device 2. This provides a safety element for a good mechanical resistance to fatigue of the device 2 that is the subject of the invention.

FIG. 12 shows how, in the prior art, the possibility of a combination of two vertebral stages, one of which has been fused and the other made mobile by the device 2.

In a possible variant applied to this device, an additional safety element is included (FIGS. 10 and 11) which is a central stop placed at the bottom of the concave cavity 220 of the fixed rod 22. During the compression forces, the piston 200 of the piston rod 20 comes into contact with the stop b after a predefined vertical movement of the order of a few millimeters, which prevents overloads which could be applied to the viscoelastic means 23.

This additional stop b can be sufficient in itself or supplement that resulting from the alignment of the end of the screw with the mark r.

The invention claimed is:

1. A dynamic posterior stabilization device, comprising:
   a fixed rod having a first end, the first end having a concave surface;
   a cap affixed to the first end of the fixed rod such that the concave surface of the first end is housed within an interior volume of the cap;
   a mobile piston having a shaft and a head end, the shaft being disposed through an orifice of the cap such that the head end of the mobile piston is housed within the interior volume of the cap;
   a viscoelastic ring disposed around the shaft of the mobile piston and between the cap and the head end of the mobile piston;
   a viscoelastic shock-absorbing pad having a convex face, the viscoelastic shock-absorbing pad being disposed between the head end of the mobile piston and the concave surface of the first end of the fixed rod such that the convex face contacts the concave surface of the first end of the fixed rod for centering the viscoelastic pad on the first end of the fixed rod without contacting the cap; and
   wherein the fixed rod has a longitudinal axis which is disposed at an oblique angle relative to a longitudinal axis of the cap.

2. The dynamic posterior stabilization device of claim 1, wherein the viscoelastic ring has a knuckle on a face of the viscoelastic ring limiting the risks of initiating a break when the mobile piston adopts an angle, said viscoelastic ring also making it possible to apply an elastic return force to the angular ranges of movement of the shaft of the mobile piston by deformation of the viscoelastic ring.

3. The dynamic posterior stabilization device of claim 1, wherein the mobile piston comprises a mark for positioning the device within a head of a pedicular screw; wherein the mark is configured to indicate a pre-determined distance between the cap and the head of the pedicular screw.

4. The dynamic posterior stabilization device of claim 1, wherein it comprises a stop placed at the center of the concave surface of the fixed rod which, during the compression forces, causes the head end of the mobile piston the piston rod (20) to come into contact with this stop after a vertical movement.

5. The dynamic posterior stabilization device of claim 1, wherein the convex face of the viscoelastic shock-absorbing pad and the concave surface of the fixed rod are concentric and match, which allows centering with the cap so that the viscoelastic shock-absorbing pad is perfectly centered inside the cap allowing the viscoelastic shock-absorbing pad to deform without coming into contact with the internal walls of the cap while preventing friction and excess stresses that are extremely harmful to the longevity of the viscoelastic shock-absorbing pad.

6. The dynamic posterior stabilization device of claim 1, wherein the orifice of the cap has a frustoconical shape and wherein the orifice is configured such that the shaft of the mobile piston is angularly moveable through a range of 0-15° with respect to an axis perpendicular to the orifice.

\* \* \* \* \*

UNITED STATES PATENT AND TRADEMARK OFFICE
CERTIFICATE OF CORRECTION

| | | |
|---|---|---|
| PATENT NO. | : 9,072,544 B2 | Page 1 of 1 |
| APPLICATION NO. | : 12/993976 | |
| DATED | : July 7, 2015 | |
| INVENTOR(S) | : Fortin et al. | |

It is certified that error appears in the above-identified patent and that said Letters Patent is hereby corrected as shown below:

Title page, item (57) should read:

--(57)  ABSTRACT

A device is provided for dynamic posterior stabilization. The device includes a mobile piston rod with a piston head at an end thereof; a viscoelastic shock-absorbing unit having a convex surface; a fixed rod defining an angle relative to an axis of a casing and the fixed rod including, at an end thereof, a concave surface; a viscoelastic ring; and wherein the viscoelastic components are contained within the casing.--

In the claims:

Column 6, line 31, should read:

--causes the head end of the mobile piston to--

Signed and Sealed this
Third Day of November, 2015

Michelle K. Lee
*Director of the United States Patent and Trademark Office*